United States Patent
Houze et al.

(10) Patent No.: US 9,869,621 B2
(45) Date of Patent: Jan. 16, 2018

(54) TEST BENCH COMBINING HIGH-FREQUENCY TRIBOLOGICAL STRESS AND OLIGOCYCLIC FATIGUE, ON A BLADE DISK OF TURBOSHAFT ENGINE OF AN AIRCRAFT INCLUDING A TEST PIECE HAVING A PORTION WITH A SHAPE OF A BLADE ROOT OF A ROTOR AND IS ENGAGED IN A GROOVE SHAPE COMPLEMENTARY TO ANOTHER TEST PIECE

(71) Applicants: Turbomeca, Bordes (FR); SNECMA, Paris (FR)

(72) Inventors: Laurent Houze, Andoins (FR); Jean Philippe Lapuyade, Monein (FR); Franck Vernis, Mirepeix (FR); François Vogel, Ousse (FR); Jean Vincent Manuel Meriaux, Moissy-Cramayel (FR)

(73) Assignees: TURBOMECA, Bordes (FR); SNECMA, Paris (FR)

( * ) Notice: Subject to any disclaimer, the term of this patent is extended or adjusted under 35 U.S.C. 154(b) by 0 days.

(21) Appl. No.: 14/890,831

(22) PCT Filed: May 9, 2014

(86) PCT No.: PCT/FR2014/051073
§ 371 (c)(1),
(2) Date: Nov. 12, 2015

(87) PCT Pub. No.: WO2014/184469
PCT Pub. Date: Nov. 20, 2014

(65) Prior Publication Data
US 2016/0116387 A1    Apr. 28, 2016

(30) Foreign Application Priority Data
May 17, 2013    (FR) ...................... 13 54439

(51) Int. Cl.
*G01N 3/32*    (2006.01)
*G01N 3/04*    (2006.01)

(52) U.S. Cl.
CPC ....... *G01N 3/32* (2013.01); *G01N 2203/0005* (2013.01); *G01N 2203/0073* (2013.01);
(Continued)

(58) Field of Classification Search
CPC ... G01L 9/0054; G01L 19/141; G01L 9/0073; B81B 7/0058; B81B 2201/0264;
(Continued)

(56) References Cited

U.S. PATENT DOCUMENTS

2002/0017144 A1* 2/2002 Miles ..................... G01N 3/32
                                                                        73/808
2005/0268728 A1* 12/2005 Phipps .................... G01N 3/04
                                                                        73/826

FOREIGN PATENT DOCUMENTS

| EP | 1 602 914 A2 | 12/2005 |
| FR | 2 963 425 A1 | 2/2012 |
| SU | 712734 A1 | 1/1980 |

OTHER PUBLICATIONS

International Search Report dated Jul. 11, 2014, issued in corresponding International Application No. PCT/FR2014/051073, filed May 9, 2014, 2 pages.
(Continued)

*Primary Examiner* — Lisa Caputo
*Assistant Examiner* — Brandi Hopkins
(74) *Attorney, Agent, or Firm* — Christensen O'Connor Johnson Kindness PLLC

(57) ABSTRACT

A test rig combining high-frequency tribological stress and low-cycle fatigue. The test rig includes a first test piece which is fixed to a frame and defines at least one bearing surface, a second test piece which is connected to an actuator
(Continued)

for loading the second test piece so that it bears against the at least one bearing surface of the first test piece, a heater configured for heating the test pieces and a vibration generator, such as a shaker, for loading the test pieces in a vibratory manner so as to carry out a fretting fatigue and low-cycle and high-cycle fatigue test. One of the test pieces includes a portion in the shape of a turbine engine rotor blade root and which is inserted in a groove having a shape that is substantially complementary to the other test piece so as to reproduce a turbine engine blade-disc attachment.

9 Claims, 3 Drawing Sheets

(52) U.S. Cl.
CPC .................. *G01N 2203/027* (2013.01); *G01N 2203/0226* (2013.01)

(58) Field of Classification Search
CPC ..... B81B 2207/015; H01L 2224/48091; H01L 2224/48247; H01L 2924/1815; H01L 2924/00014; H01L 2224/48465; H01L 2924/00; H01L 2924/1461; H01L 2924/3025; H01L 2224/45144; H01L 2924/15747; H01L 2924/181; B81C 1/00309; B81C 2203/0154; Y10T 29/49126
USPC .................................. 73/721, 715–717, 727
See application file for complete search history.

(56) References Cited

OTHER PUBLICATIONS

Written Opinion of the International Searching Authority dated Jul. 11, 2014, issued in corresponding International Application No. PCT/FR2014/051073, filed May 9, 2014, 7 pages.
International Preliminary Report on Patentability dated Nov. 17, 2015, issued in corresponding International Application No. PCT/FR2014/051073, filed May 9, 2014, 1 page.

\* cited by examiner

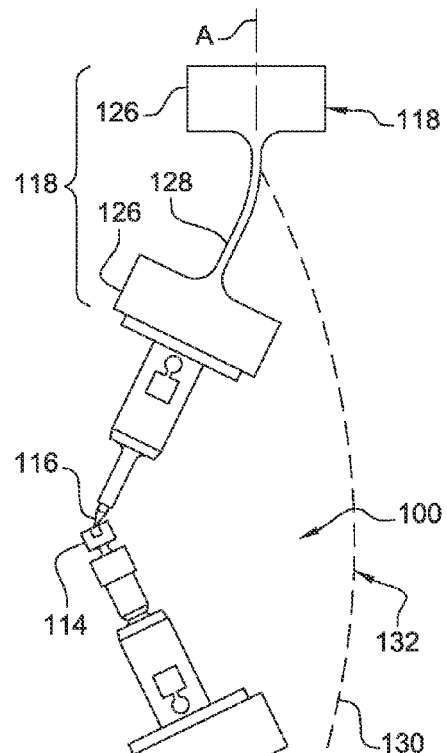
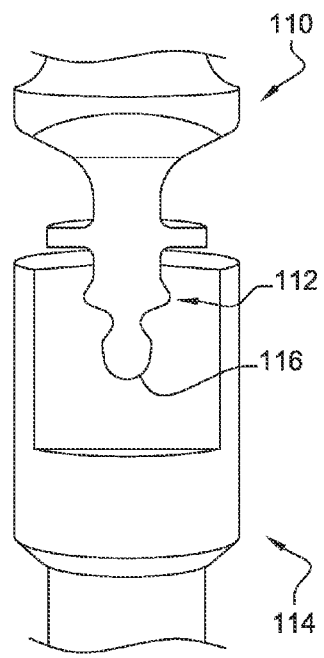
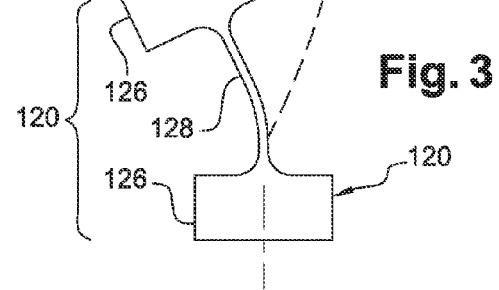
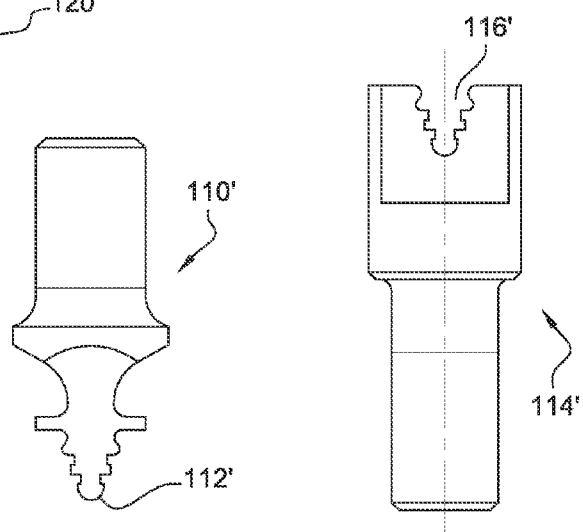
Fig. 3
Fig. 4
Fig. 5
Fig. 6

TEST BENCH COMBINING HIGH-FREQUENCY TRIBOLOGICAL STRESS AND OLIGOCYCLIC FATIGUE, ON A BLADE DISK OF TURBOSHAFT ENGINE OF AN AIRCRAFT INCLUDING A TEST PIECE HAVING A PORTION WITH A SHAPE OF A BLADE ROOT OF A ROTOR AND IS ENGAGED IN A GROOVE SHAPE COMPLEMENTARY TO ANOTHER TEST PIECE

TECHNICAL FIELD

The present invention relates to a test rig combining high-frequency tribological stresses and low-cycle fatigue, also known by the name fretting fatigue test, said test rig being intended to reproduce a turbine engine blade-disc attachment.

PRIOR ART

Numerous turbine engine parts are subjected to complex stresses superimposing high-cycle (vibratory) and low-cycle stresses. The characterisation becomes very complex when tribological stress is added, such as for a blade-disc attachment.

This is the case for a turbine blade, which is loaded with a centrifugal force due to the rotation of the turbine, a vibratory force due to the environment and the resonating thereof. These two stresses lead to sliding of the blade root against the lateral projections of the recess in the disc, in which recess the blade root is inserted. Knowledge of this tribological aspect is essential because the blade root is then subjected to fretting fatigue damage. This field of stress is still largely unstudied, but knowledge thereof and dealing with the related risks are a major concern for the coming years.

In order to correct this deficiency, said contacts are characterised and studied by means of very simple tests at frequencies which are very different from those experienced by the parts of the turbine engine, sometimes even at much lower temperatures by loading the contact surfaces only with a simple alternating sliding cycle whilst several types of stress are superimposed.

In the context of the study of fretting fatigue damage, a distinction is made in the current art between two different families of experimental means:

1) fretting fatigue tests which are referred to as conventional, aimed at an in-depth study of the contact with perfect control of the local conditions applied to the contact between the test pieces. In general, these tests use a large number of instruments and make it possible to access significant tribological parameters (displacement, friction coefficient, etc.), and 2) technological fretting fatigue tests, aimed at getting as close as possible to the application and the stress to be studied. Compared with the above tests, these tests are not as instrument-based but become more representative.

Conventional fretting fatigue tests are carried out on test pieces having a standard geometry which are remote from the blade/disc attachment application and do not make it possible to combine the stresses described previously. Generally used are test means which are capable of reaching maximum frequencies of 100 Hz and do not combine low-cycle and high-cycle cycles at high temperature.

When the test means aim to reproduce a contact geometry similar to a blade-disc attachment, generally of the one-lobe type, said means are also limited in terms of combining the stresses. Said test means are also not configured to combine low-cycle and high-cycle cycles at high temperature.

The test means from the prior art, even those dedicated to fretting fatigue and fatigue tests, thus do not make it possible to reliably analyse a turbine engine blade-disc attachment which is representative of an actual attachment in operating conditions.

The aim of the present invention is in particular to provide a simple, effective and economical solution to this problem.

SUMMARY OF THE INVENTION

The invention proposes a test rig combining high-frequency tribological stress and low-cycle fatigue, comprising a first test piece which is fixed to a frame and defines at least one bearing surface, and a second test piece which is connected to traction means for loading the second test piece so that it bears against the or each bearing surface of the first test piece and carrying out a low-cycle fatigue test, one of the test pieces comprising a portion which is in the shape of a turbine engine rotor blade root and is inserted in a groove, the shape of which groove is substantially complementary to the other test piece so as to reproduce a turbine engine blade-disc attachment, the rig further comprising a heater configured for heating the test pieces and means for loading the test pieces in a vibratory manner so as to carry out a fretting fatigue test, and being characterised in that in that it comprises means for adjusting the position of the test pieces around an axis which is parallel to the tensile axis, and means for locking said test pieces in a position around said axis.

The test piece having the portion which is in the shape of a blade root is for example connected to the traction means, and the other test piece comprising the groove is then fixed to the frame.

The invention aims to propose a new experimental test rig by making it possible to characterise a blade-disc attachment which is subjected to fretting fatigue stress, combining a low-cycle cycle representing a powered flight (centrifugal force), a high-cycle cycle representing the vibrations generated by the operation of the aircraft and the engine whilst ensuring sliding between the bearing surfaces. A defining feature of the invention is that of making it possible to get as close as possible to the vibratory stress modes of the blade which are sometimes complex and at high frequencies, as well as actual temperature conditions of use of the blade, whilst ensuring and controlling sliding in the contact regions.

Lastly, the ability to adjust and lock the position of the test pieces around an axis which is parallel to the tensile axis makes it possible to adjust the loading direction and, as a result, to achieve complex resonance modes which can combine for example bending and torsion.

The invention thus makes it possible to reproduce as closely as possible the conditions experienced by a rotor blade during operation.

The test pieces can be made of the same or different materials. In the case in which the test pieces are made of different materials, the test rig makes it possible to characterise the pairs of material in contact.

The heater is configured to heat the test pieces to a temperature of approximately 800° C., that is to say to a temperature representing the actual conditions of use of a turbine engine rotor blade root.

Advantageously, the test rig is configured in such a way that the portion which is in the shape of a blade root of the first test piece and the groove in the second test piece are located in an antinode of a first vibration mode of the rig. This makes it possible to maximise the sliding and deformation amplitudes of the test pieces.

The portion in the shape of a blade root preferably has a shape and dimensions which are similar to those of an actual turbine engine rotor blade, so as to reproduce as faithfully as possible a blade-disc attachment. The test pieces can be sized so as to be compatible with sizes of available single-crystal blanks. This makes it possible to characterise said single crystals and to envisage studying machining and geometrical parameters on the behaviour of a pair of materials (the effect of the plays in the blade-disc attachment, superficial metallurgical health, etc.). The test piece comprising the groove is preferably rigid enough to prevent too great a deformation thereof as a result of the significant mechanical stresses to which said test piece is subjected.

The loading means can comprise a shaker which loads a portion of the rig to a frequency of approximately 2000 Hz, and preferably of between 1000 and 2000 Hz. The rig thus makes it possible to work at high frequencies which are similar to the natural frequencies of a rotor blade. The natural frequencies of the test pieces can be modified by resizing the excitation means in a suitable manner.

Advantageously, one of the test pieces is connected to the frame by an I-shaped part having a flexible middle portion, and the other test piece is connected to the traction means by another I-shaped part having a flexible middle portion. The I-shaped parts are intended to be excited by the loading means. By calculating and adapting the moment of inertia thereof in the direction of the vibratory excitation, it is possible to modify the natural modes of the anchoring line and to thus sweep very wide operating areas of the blade-disc attachment.

The adjustment and locking means can comprise screws which are likewise used to fix the test pieces to the I-shaped parts.

The portion of the test piece which is in the shape of a blade root can be of the dovetail (one-lobed) or fir-tree (three-lobed) type.

The present invention also relates to a method for using a rig for fretting fatigue and fatigue tests, said test rig comprising a test piece which is connected to traction means and comprises a portion which is in the shape of a turbine engine rotor blade root, and another test piece which is fixed to a frame and comprises a groove for receiving said portion in the shape of a blade root, said groove being substantially complementary to said portion and defining at least one bearing surface of said portion, comprising a step consisting in simultaneously subjecting the two test pieces to heating and to tensile and vibratory stresses for a fretting fatigue and low-cycle and high-cycle fatigue test. The method is characterised in that it comprises, before the preceding step, a step of adjusting and locking the position of the test pieces around an axis which is parallel to the tensile axis.

DESCRIPTION OF THE DRAWINGS

The invention will be better understood, and other details, features and advantages of the invention will become apparent upon reading the following description, given by way of non-limiting example and with reference to the accompanying drawings, in which:

FIG. 3 is a schematic view of another test rig according to the invention, FIG. 4 is a partial schematic perspective view of the test pieces of a test rig according to the invention, FIGS. 5 and 6 are schematic perspective views of the test pieces from FIG. 4.

DETAILED DESCRIPTION

Figure 1:
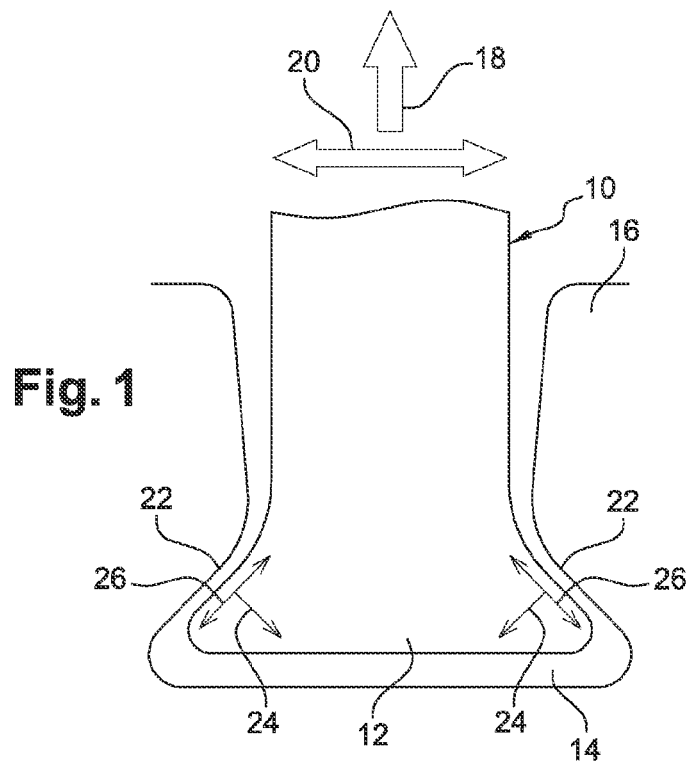
FIG. 1 is a very schematic view of the attachment of a blade root in a groove of a rotor disc of a turbine engine.

Reference is firstly made to FIG. 1, which schematically shows a blade-disc attachment of a turbine engine, the blade 10 being a rotor blade comprising a root 12 which is inserted in a groove 14 in the periphery of a disc 16, said disc comprising an annular array of grooves 14 of this type for receiving the roots of a plurality of blades. The assembly formed by the disc 16 and the blades 10 form a rotor wheel for example of a turbine of the turbine engine. In this case, the root 12 is of the dovetail type.

During operation, the blade 10 is subjected to centrifugal forces (arrow 18) and the vane thereof has a tendency to oscillate (arrow 20), causing the lateral portions, referred to as threads of the blade root 12, to bear and slide against lateral projections 22 of the groove 14 in the disc. The arrows 24 show normal forces which are applied to the surfaces facing the blade root 12 and the groove 14, and the arrows 26 denote shearing forces which are applied to said surfaces.

Figure 2:
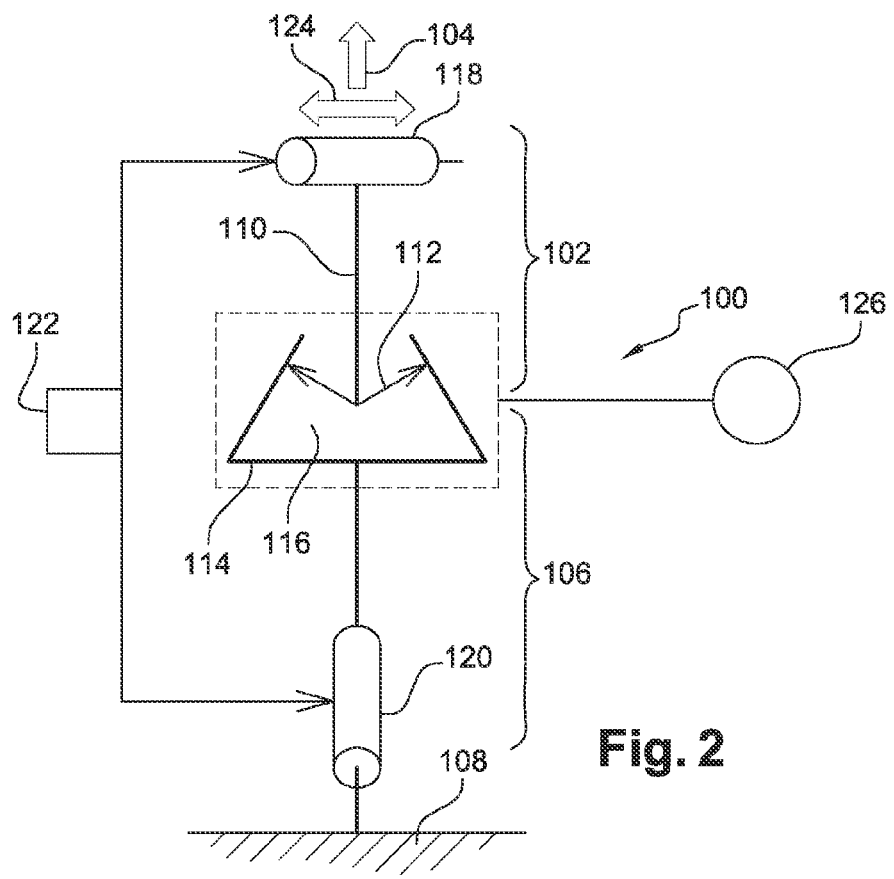
FIG. 2 is a very schematic view of a test rig according to the invention.

FIG. 2 schematically shows an embodiment of a test rig according to the invention, which is designed to reproduce a blade-disc attachment which is subjected to low-cycle fatigue (LCF) and high-cycle fatigue (HCF) loading.

The test rig 100 comprises a first portion 102 which is connected to traction means (arrow 104) and a second portion 106 which is connected to a fixed frame 108.

The first portion 102 comprises a male test piece 110 which comprises a portion 112 which is shaped into a blade root and which is connected to the traction means. Said traction means comprise for example an actuator, the free end of the rod of which is connected to the test piece 110, and the cylinder of which is supported by a fixed portion of the test rig 100. Said actuator is preferably oriented in parallel with an extension axis of the male test piece 110 and is intended to reproduce the centrifugal forces to which a rotor blade is subjected during operation.

The second portion 106 of the test rig 100 comprises a female test piece 114 comprising a groove 116 for inserting the above-mentioned portion 112 of the test piece 110.

At least one of the means 118, 120 for connecting the male test piece 110 to the traction means and the female test piece 114 to the frame 108 is loaded by excitation means 122, such as a shaker, which is intended to subject the blade-disc attachment to high-frequency vibrations (1000 Hz-2000 Hz—arrow 124) which are intended to reproduce the vibrations to which a rotor blade is subjected during operation. In addition, the test rig according to the invention comprises a heater 126 for heating the blade-disc attachment to a temperature of for example 800° C.

As can be seen in FIG. 3, each of the connection means comprises an I-shaped part 118, 120. Each part 118, 120 comprises two parallel, substantially parallelepipedal, solid blocks 126 which are interconnected by a flexible wall 128 which is perpendicular to the blocks. The female test piece 114 is applied and fixed by screws to one of the blocks 126 of the part 120, the other block 126 of which is fixed to the frame 108, and the male test piece 110 is applied and fixed by screws to one of the blocks 126 of the part 118, the other block 126 of which is fixed to the traction means. The flexible walls 128 of the I-shaped parts are substantially coplanar.

FIG. 3 schematically shows the test rig 100 which is deformed according to a first vibration mode 120. Advantageously, as can be seen in this drawing, the blade-disc attachment is located in the region of a vibration antinode 132 of this first mode, in such a way that the slidings between the male test piece and the female test piece have a maximum amplitude.

In order to achieve high frequencies, the invention can use a shaker which is coupled to the anchoring line of the male test piece 110. The principal of the test is thus to seek the natural frequencies of the system in order to have the highest amount of energy in the region of the contact, to reach high frequencies (up to 2000 Hz) and to ensure relative sliding between the test pieces. The natural frequencies and the amplitudes can be shifted by changing the moment of inertia of the I-shaped parts 118, 120 in the direction of excitation.

The defining feature is to be able, whilst working at high temperatures which are representative of the intended applications, to finely change the sliding conditions by modifying the rigidity of the anchoring line in order to shift the natural modes and to change the sliding direction.

To do this, the anchoring line and the excitation thereof have been studied in order to operate the contact in a maximum amount of deformation due to the vibratory stress.

FIGS. 4 to 6 show first embodiments of the blade-disc attachment and in particular of the male test piece 110, 110' and the female test piece 114, 114' of the rig 100. In said embodiments, the portion 112, 112' of the male test piece which is shaped into a blade root is of the fir-tree type, the portion 112 of the male test piece from FIG. 4 being of the two-lobe fir-tree type and that 112' from FIG. 5 being of the three-lobe fir-free type. FIG. 6 shows a female test piece 114' comprising a groove 116', the shape of which is complementary to the portion 112' of the male test piece from FIG. 5.

The portion 112, 112' of the male test piece 110, 110' is mounted with a small amount of play in the groove 116, 116' of the female test piece, as is the case in an actual blade-disc attachment.

Figure 7:
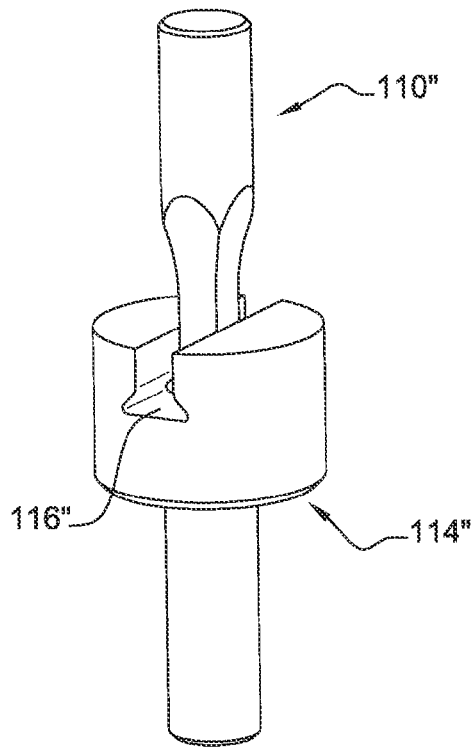
FIG. 7 is a schematic perspective view of the test pieces of another test rig according to the invention.
Figure 8:
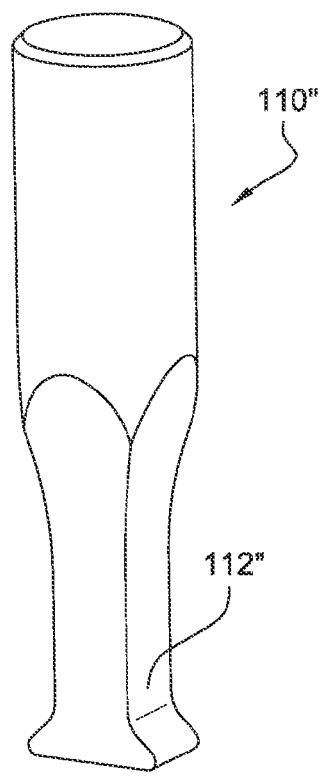
FIG. 8 is a schematic perspective view of one of the test pieces from FIG. 7.

In the variant in FIGS. 7 and 8, the portion 112" of the male test piece 110" which is shaped into a blade root is of the dovetail type, and the female test piece 114" comprises a groove 116", the shape of which is complementary to said portion 112".

Figure 9:
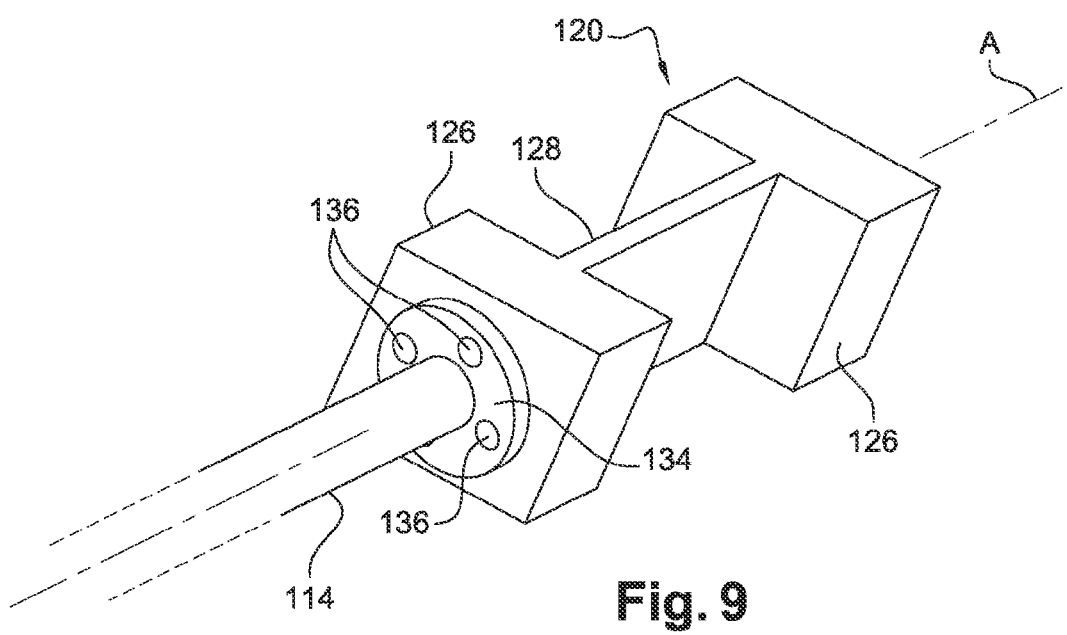
FIG. 9 is a schematic perspective view of the means for fixing a test piece to an I-shaped part of the rig from FIG. 3.

The test pieces can each comprise a cylindrical body, as is shown in FIGS. 7 and 8. Each of said bodies can be fixed to or rigidly connected to a plate for fixing to an I-shaped part 118, 120. FIG. 9 shows the plate 134 for fixing the female test piece 114 to the I-shaped part 120, the plate for fixing the male test piece 110 to the other I-shaped part 118 being able to be identical to this plate.

The plate 134 has a circular contour and comprises holes for screws 136 for fixing the female test piece which are intended to be screwed into threaded holes in a block 126 of the I-shaped part 120.

Advantageously, and as explained above, the position of the blade-disc attachment around the tensile axis A can be adjusted and locked, for example by means of the screws 136. For this purpose, the screws 136 are preferably mounted with play in the holes in the plate 134 so as to allow angular displacement, for example of a few degrees, around the axis A of the female test piece 114 and the plate 134, when the screws 136 are loose. Tightening the screws 136 ensures the locking of the female test piece 114 and the plate 134 in this position. The male test piece 110 and the fixing plate thereof are advantageously mounted in the same manner, that is to say in an adjustable manner around the axis A with respect to the I-shaped part 118 to which they are fixed. In practice, so as not to force the blade-disc attachment before the start of a test, the position of the male test piece 110, the female test piece 114, and the fixing plates thereof around the axis A is adjusted, the angular shifts of the male test piece 110 and the female test piece 114 around the axis A being of the same value and in the same direction.

The invention presented here makes it possible to reproduce the different stresses experienced by a blade being able to have an effect on the behaviour of the attachment in the case of fretting fatigue. This makes it possible to ensure perfect reproducibility of the application and paves the way for studying numerous parameters so as to be able to determine the respective weights thereof and the conceivable areas for improvement. One of the defining features of the invention is that it makes it possible to adjust complex parameters to be implemented, such as the frequency level, the amplitude of the LCF cycles and the combination of complex natural modes, as a result of the modification of the I-shaped parts and the possible orientation thereof with respect to the axis of vibratory stress. In the example in FIG. 3, the direction of vibratory excitation (arrow 140) is perpendicular to the bearing surfaces between the male test piece and the female test piece. Modifying this orientation (which is permitted by the above-mentioned screws 136) makes it possible to achieve complex natural modes which superimpose bending and torsion.

The invention claimed is:

1. Test rig combining high-frequency tribological stress and low-cycle fatigue, comprising;
   a first test piece fixed to a frame and defining at least one bearing surface;
   a second test piece connected to traction means for loading the second test piece so that it bears against the at least one bearing surface of the first test piece and carrying out a low-cycle fatigue test, wherein one of the first and second test pieces comprising a portion configured in the shape of a turbine engine rotor blade root and the other one of the first and second test piece includes a groove, having a shape that is complementary to the said portion so as to reproduce a turbine engine blade-disc attachment,
   a heater configured for heating the test pieces;
   means for loading the first and second test pieces in a vibratory manner so as to carry out a fretting fatigue test;
   means for adjusting the position of the first and second test pieces around an axis which is parallel to a tensile axis; and
   means for locking said first and second test pieces in a position around said axis which is parallel to the tensile axis,
   wherein the adjustment means and the locking means are configured for adjusting the vibratory loading direction.

2. Test rig according to claim 1, wherein the heater is configured to heat the first and second test pieces to a temperature of approximately 800.degree. C.

3. Test rig according to claim 1, wherein the test rig is configured such that the portion in the shape of a blade root of the one of the first and second test pieces and the groove in the other one of the first and second test pieces are located in an antinode of a first vibration mode of the test rig.

4. Test rig according to claim 1, wherein the portion in the shape of a blade root has a shape and dimensions which are similar to those of an actual turbine engine rotor blade.

5. Test rig according to claim 1, wherein the loading means comprise a shaker which loads a portion of the rig to a frequency of approximately 2000 Hz.

6. Test rig according to claim 1, wherein one of the test pieces is connected to the frame by an I-shaped part having a flexible middle portion, and the other test piece is connected to the traction means by another I-shaped part having a flexible middle portion.

7. Test rig according to claim 6, wherein the adjustment means and the locking means comprise screws configured to fix the test pieces to the I-shaped parts.

8. Test rig according to claim 1, wherein the portion in the shape of a blade root is of the dovetail or fir-tree type.

9. Method for using a test rig for fretting fatigue and fatigue tests, said test rig comprising a first test piece that comprises a portion configured in the shape of a turbine engine rotor blade root, and a second test piece fixed to a frame and comprises a groove for receiving said portion in the shape of a blade root, said groove being complementary to said portion and defining at least one bearing surface of said portion, the method comprising:

adjusting and locking the position of the first and second test pieces around an axis parallel to a tensile axis;

simultaneously subjecting the first and second test pieces to heating and to tensile and vibratory stresses for a fretting fatigue and low-cycle and high-cycle fatigue test.

* * * * *